(12) United States Patent
Zhou et al.

(10) Patent No.: US 11,053,191 B2
(45) Date of Patent: Jul. 6, 2021

(54) HYDROXY FUNCTIONAL ALKYL CARBAMATE CROSSLINKERS

(71) Applicant: PPG Industries Ohio, Inc., Cleveland, OH (US)

(72) Inventors: Hongying Zhou, Allison park, PA (US); William Retsch, Allison Park, PA (US); Jonathan Breon, Pittsburgh, PA (US); Christopher P. Kurtz, Millvale, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 15/865,348

(22) Filed: Jan. 9, 2018

(65) Prior Publication Data

US 2019/0210962 A1    Jul. 11, 2019

(51) Int. Cl.
| | |
|---|---|
| *C07C 271/16* | (2006.01) |
| *C08K 5/205* | (2006.01) |
| *C09D 7/63* | (2018.01) |
| *C09D 123/00* | (2006.01) |
| *C09D 175/04* | (2006.01) |
| *C07C 271/40* | (2006.01) |
| *C08K 5/00* | (2006.01) |
| *C08L 75/04* | (2006.01) |
| *C08G 18/28* | (2006.01) |
| *C09D 133/08* | (2006.01) |
| *C08G 18/32* | (2006.01) |
| *C08G 18/75* | (2006.01) |

(52) U.S. Cl.
CPC .......... *C07C 271/16* (2013.01); *C07C 271/40* (2013.01); *C08G 18/284* (2013.01); *C08G 18/2815* (2013.01); *C08G 18/3275* (2013.01); *C08G 18/755* (2013.01); *C08K 5/0025* (2013.01); *C08K 5/205* (2013.01); *C08L 75/04* (2013.01); *C09D 7/63* (2018.01); *C09D 123/00* (2013.01); *C09D 133/08* (2013.01); *C09D 175/04* (2013.01)

(58) Field of Classification Search
CPC ... C07C 269/04; C07C 271/16; C07C 271/40; C07C 271/42; C08K 5/0025; C08K 5/205; C08L 71/00; C08L 71/02; C08L 71/08; C08L 75/04; C09D 7/63; C09D 123/00; C09D 175/04; C09D 171/00; C09D 171/02; C09D 171/08; C09D 5/033; C08G 59/4057
USPC .......... 252/182.13, 182.23, 182.24, 192.25; 560/24, 25, 115
See application file for complete search history.

(56) References Cited

U.S. PATENT DOCUMENTS

| | | | | |
|---|---|---|---|---|
| 2,528,399 A | * | 10/1950 | Strain | ................... C07C 271/06 524/199 |
| 3,553,254 A | * | 1/1971 | Tesoro | ................ D06M 15/423 252/8.61 |
| 4,484,994 A | | 11/1984 | Jacobs, III et al. | |
| 4,520,167 A | | 5/1985 | Blank et al. | |
| 4,758,632 A | | 7/1988 | Parekh et al. | |
| 4,820,830 A | | 4/1989 | Blank | |
| 5,134,205 A | | 7/1992 | Blank | |
| 5,292,833 A | | 3/1994 | Grahe et al. | |
| 5,336,556 A | * | 8/1994 | Yoshida | ................ B01D 39/163 156/296 |
| 7,022,767 B2 | * | 4/2006 | Mayo | ................... C08G 18/792 252/182.27 |
| 2003/0018190 A1 | | 1/2003 | Jones | |
| 2008/0138639 A1 | | 6/2008 | Swarup et al. | |
| 2009/0074978 A1 | | 3/2009 | Ohrbom | |

FOREIGN PATENT DOCUMENTS

| | | | | | |
|---|---|---|---|---|---|
| DE | | 873543 C | * | 4/1953 | .......... C07C 271/06 |
| EP | | 0246483 A2 | | 11/1987 | |
| EP | | 0257848 A2 | | 3/1988 | |

(Continued)

OTHER PUBLICATIONS

English machine translation of Schlack DE 873543 C. (Year: 1953).*

Paramonov et al., "Fully Acid-Degradable Biocompatible Polyacetal Microparticles for Drug Delivery", Bioconjugate Chem., 2008, pp. 911-919, vol. 19, No. 4.

*Primary Examiner* — Matthew R Diaz
(74) *Attorney, Agent, or Firm* — Diane R. Meyers

(57) ABSTRACT

A hydroxy functional alkyl carbamate is disclosed having the formula:

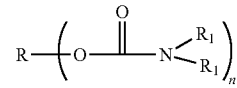

wherein R comprises a substituted or unsubstituted $C_1$ to $C_{36}$ alkyl group, an aromatic group, and/or a polymeric moiety; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6.

The present invention is also directed to a composition, and substrates coated therewith, comprising a film-forming resin; and a hydroxy functional alkyl carbamate crosslinker having the formula shown above.

Other hydroxy functional alkyl carbamate compounds, polymers made with the same, and compositions comprising the same are also disclosed as are substrates coated at least in part with or formed with any of the compositions described herein.

20 Claims, No Drawings

(56) References Cited

FOREIGN PATENT DOCUMENTS

| EP | 0570077 | B1 | | 7/1996 | | |
|---|---|---|---|---|---|---|
| EP | 0915113 | A1 | * | 5/1999 | ......... | C08G 18/6225 |
| WO | WO-0026313 | A1 | * | 5/2000 | ........... | C07D 251/34 |
| WO | 2017123955 | A1 | | 7/2017 | | |

* cited by examiner

HYDROXY FUNCTIONAL ALKYL CARBAMATE CROSSLINKERS

FIELD OF THE INVENTION

The present invention is directed to hydroxy functional alkyl carbamate crosslinkers. Coatings comprising such carbamate crosslinkers are also within the scope of the present invention, as are substrates coated at least in part with such a coating and substrates formed with such carbamates.

BACKGROUND OF THE INVENTION

Coatings are applied to numerous substrates to provide protective and/or decorative qualities. These coatings are often thermoset coatings, which cure upon reaction of a functional resin with a crosslinking agent having functionality that reacts with the functionality of the resin. Crosslinkers are often formaldehyde based. Many industries are interested in reducing if not eliminating formaldehyde in coatings. Coatings that are substantially, essentially or completely free of formaldehyde are desired. It is also desired by many industries to lower the temperature at which coatings cure. Additionally, protective qualities provided by electrostatic modification are desirable in powder coatings on substrate areas that are normally weak.

SUMMARY OF THE INVENTION

The present invention is directed to a hydroxy functional alkyl carbamate having the formula:

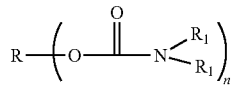

wherein R comprises a substituted or unsubstituted $C_1$ to $C_{36}$ alkyl group, an aromatic group, and/or a polymeric moiety; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6.

The present invention is also directed to a composition, and substrates coated therewith, comprising a film-forming resin; and a hydroxy functional alkyl carbamate crosslinker having the formula shown above.

DETAILED DESCRIPTION OF THE INVENTION

The present invention is directed to hydroxy functional alkyl carbamate compounds as described below. Such compounds can be used in various compositions including coatings, adhesives, and sealants, and can function as crosslinkers in such compositions. The compounds may have the general formula:

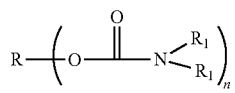

wherein R comprises a substituted or unsubstituted $C_1$ to $C_{36}$ alkyl group, an aromatic group, and/or a polymeric moiety; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6. The $R_1$ groups may exclude, that is, be free from, ether linkages.

The present invention is further directed to a composition comprising:
a. a film-forming resin; and
b. a hydroxy functional alkyl carbamate crosslinker having the formula:

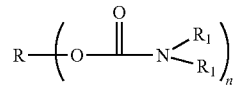

wherein R comprises a substituted or unsubstituted $C_1$ to $C_{36}$ alkyl group, an aromatic group, and/or a polymeric moiety; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6. The $R_1$ groups may exclude, that is, be free from, ether linkages.

R may comprise a polymeric moiety. A "polymeric moiety" as used herein in the context of "R" refers to any polymer or oligomer to which has been attached two to six hydroxy functional alkyl carbamate groups. The polymer can be, for example, a polyether, polyester polyurethane, a polyether polyurethane, a polyamide polyurethane, a polyurethane polyol, a polyester, and/or an acrylic polyol. The moiety can itself contain functionality, such as acid functionality, hydroxy functionality, and/or amine functionality. The polymeric moiety (which may be oligomeric as noted above) can have a number average molecular weight ("Mn") of 250 or greater, such as 500 or greater, 1000 or greater, 2500 or greater, or 4000 or greater. Mn, as used herein, refers to the number average molecular weight and means the theoretical value as determined by Gel Permeation Chromatography using Waters 2695 separation module with a Waters 410 differential refractometer (RI detector) and polystyrene standards. The Mn values reported according to the invention were determined using this method. Tetrahydrofuran (THF) was used as the eluent at a flow rate of 1 ml $min^{-1}$, and two PL Gel Mixed C columns were used for separation.

A polyether will be understood as referring to a polymer having a polyether backbone such as are characterized by propylene oxide, ethylene oxide, or mixed propylene oxide and ethylene oxide repeating units, polyTHF or polymeg. A polyurethane will be understood as referring to a polymer having urethane linkages in the backbone and may further comprise ester linkages (polyester polyurethane), amide linkages (polyamide polyurethane), and/or polyol functionality (polyurethane polyol). A polyester will be understood as referring to a polymer having ester linkages; such linkages can be formed by reaction between a polyol and a polyacid by any means known in the art. The polymeric moiety may also comprise an acrylic polyol; an acrylic polyol can be formed by reaction between one or more ethylenically unsaturated monomers by any means known in the art.

In all cases, R may be substituted or unsubstituted. R, as noted above, may comprise a substituted or unsubstituted $C_1$ to $C_{36}$ alkyl group and/or an aromatic group. For example, the alkyl group may have two to ten carbon atoms, such as six carbon atoms. The alkyl group may be derived from an isocyanate, such as a diisocyanate. Suitable examples include isophorone diisocyanate and hexamethylene isocyanate. The aromatic group may be derived from an aromatic ring containing isocyanate, suitable examples of which include methylene diphenyl diisocyanate, toluene diisocyanate and tetramethylxylylene diisocyanate. "Derived from" can mean the residue of the isocyanate that remains after reaction with another compound.

It will be appreciated that the hydroxy functional alkyl carbamates of the present invention are monomeric in nature. This is the case even if R represents a polymeric moiety. The R group may contain substitutions, such as functional groups. The R group may also exclude, that is, be free from, one or more type of functional groups, such as hydroxy groups and/or epoxy groups.

It will also be appreciated that the hydroxy functional alkyl carbamates of the present invention are multifunctional; that is, they have two to six hydroxy functional carbamate groups. The present carbamates can therefore function as crosslinkers in a coating composition. Thus, the present carbamates are distinct from other carbamates in the art that are only monofunctional (i.e. that have only one functional carbamate group), as those carbamates, although reactive, cannot function as crosslinkers. The present carbamates are also distinct from other carbamates having the structure

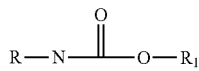

as the present carbamates are more reactive at lower temperatures.

Certain hydroxy functional alkyl carbamates of, and/or used according to, the invention may be made by reacting a compound having a carbonyl group with an amino alcohol. Any suitable compound having a carbonyl group, such as a chloroformate or a cyclic carbonate, can be used. It will be appreciated that the "R" group will reflect the compound having a carbonyl group selected. Similarly, any amino alcohol having two or more carbon atoms can be used, and the "$R_1$" group will reflect the amino alcohol and/or carbonyl-containing compound selected. The amino alcohol and/or carbonyl-containing compound can have one, two or more hydroxyl functional groups. One or more amino alcohols and/or carbonyl-containing compounds can be used, which will result in different $R_1$ groups being present on the carbamate. $R_1$ can also be hydrogen or an alkyl group. Suitable amino alcohols include monoethanol amine, diethanol amine, diispropanol amine and methyl ethanol amine. Suitable carbonyl-containing compounds include chloroformates or cyclic carbonates.

Generally, the hydroxyl functional alkyl carbamates can be made by reacting amino alcohol and carbonyl-containing compound in an organic solvent, such as MIBK, MEK and the like. The equivalent ratio of amine to carbonyl carbons can be 2-1:1-2, such as 1:1.

The Mn of the hydroxy functional alkyl carbamate can be 100 or greater, such as 350 or greater, or 1,000 or greater, and/or can be 10,000 or lower, 6,000 or lower, 3,000 or lower, or 2,000 or lower.

The present invention is further directed to a composition comprising a film-forming resin and any of the hydroxy functional alkyl carbamate compounds described above. The composition can be, for example, a coating, an adhesive or a sealant. It will be appreciated that coatings, sealants and adhesives often comprise similar components but are formulated differently depending on the needs of the user. "Film-forming" means that the composition, upon drying and/or curing, can form a continuous film on a surface.

For example, any of the hydroxy functional alkyl carbamates as described herein may react with a film-forming resin to form a cured composition. For example, in a coating the carbamate may act as a crosslinking agent and react with the film-forming resin to form a cured coating. Accordingly, the compositions of the present invention can achieve cure without formaldehyde-based crosslinking agents. "Formaldehyde-based crosslinking agents" will be understood as those made by reacting amino compounds with formaldehyde followed by esterification with alkanols. Examples include melamine formaldehyde crosslinkers, like hexamethylol melamine and trimethylol melamine, and aminoplast crosslinkers. When used as a crosslinker, the hydroxy functional alkyl carbamate may be used alone or in combination with one or more additional crosslinkers known in the art to crosslink, for example, with functionality on the film-forming resin. One skilled in the art can select an appropriate crosslinker based on this functionality from known crosslinkers such as melamine, phenolic, carbodiimide, hydroxyalkylamide, isocyanate, blocked isocyanate, benzaguanamine, triglycidyl isocyanurate ("TGIC"), epoxies, oxazolines, and the like.

Any film-forming resin that will react with the hydroxy functional alkyl carbamate can be used according to the present invention. The film-forming resin can comprise, for example, acrylic polymers, polyester polymers, polyurethane polymers, polyamide polymers, polyether polymers, polysiloxane polymers, copolymers thereof, and mixtures thereof. Generally, these polymers can be any polymers of these types made by any method known to those skilled in the art. Such polymers may be solvent-borne or water-dispersible, emulsifiable, or of limited water solubility. The functional groups on the film-forming resin may be selected from any of a variety of reactive functional groups including, for example, carboxylic acid groups, amine groups, epoxide groups, hydroxyl groups, thiol groups, carbamate groups, amide groups, urea groups, isocyanate groups (including blocked isocyanate groups) mercaptan groups, and combinations thereof. The film-forming resin can comprise an acid functional polyester resin and/or an acid functional acrylic resin. Appropriate mixtures of film-forming resins may also be used in the preparation of the present compositions, as can additional crosslinkers as noted above. A particularly suitable film-forming resin may be a polyolefin, such as an acid functional polyolefin, a suitable example of which is an ethylene acrylic acid copolymer commercially available from Dow as PRIMACOR 5890I, or the polyolefin can be in dispersion form, such as is taught in United States Patent Application Publication Number 2016/0280951 A1 at paragraph 5 or those prepared as described in WO Number 2013/191825 A1, page 14, line 16 through page 15, line 23 and in the examples.

The composition can comprise, for example, 10 weight percent or greater of film-forming resin, such as 50 weight percent or greater or 75 weight percent or greater and/or can comprise 99 weight percent or lower of film-forming resin, such as 80 weight percent or lower or 70 weight percent or lower, with weight percent based on total solid weight of the composition. The composition can comprise, for example, 0.5 weight percent or greater of hydroxy functional alkyl carbamate crosslinker, such as 2 weight percent or greater or 7 weight percent or greater, and/or can comprise 50 weight percent or lower hydroxy functional alkyl carbamate, such as 30 weight percent or lower or 15 weight percent or lower, with weight percent based on total solid weight of the composition.

The compositions of the present invention may comprise more than one of any of the hydroxy functional alkyl carbamates described herein. For example, a composition might comprise both a hydroxyl functional alkyl carbamate with an R group having polyether urethane and with an R group having polyester urethane. A particularly suitable such composition is one in which the R comprises an acrylate functionality as well.

The composition may comprise one or more solvents including water or organic solvents. Suitable organic solvents include glycols, glycol ether alcohols, alcohols, ketones, and aromatics, such as xylene and toluene, acetates, mineral spirits, naphthas and/or mixtures thereof. "Acetates" include the glycol ether acetates. The solvent can be a non-aqueous solvent. "Non-aqueous solvent" and like terms means that less than 50% of the solvent is water. For example, less than 10%, or even less than 5% or 2%, of the solvent can be water. It will be understood that mixtures of solvents, including or excluding water in an amount of less than 50%, can constitute a "non-aqueous solvent". The composition may be aqueous or water-based. This means that 50% or more of the solvent is water. These embodiments have less than 50%, such as less than 20%, less than 10%, less than 5% or less than 2% solvent.

The composition may be in solid particulate form, i.e. a powder coating. Such coatings will be appreciated as being environmentally friendly, as only water is released on cure.

The compositions of the present invention may further comprise a catalyst. Any catalyst typically used to catalyze crosslinking between a hydroxyl group and an acid or isocyanate may be used. Examples of such a catalyst include those having metal complexes with metals such as zinc, zirconium, titanium and tin and other Lewis acids. Amines, including guanamines, may also be used. The use of a catalyst, it will be appreciated, causes the cure of the coating to occur faster.

If desired, the compositions can comprise other optional materials well known in the art of formulating, such as colorants, plasticizers, abrasion resistant particles, anti-oxidants, hindered amine light stabilizers, UV light absorbers and stabilizers, surfactants, flow control agents, thixotropic agents, fillers, organic cosolvents, reactive diluents, catalysts, grind vehicles, slip agents, moisture scavenger and other customary auxiliaries.

As used herein, the term "colorant" means any substance that imparts color and/or other opacity and/or other visual effect, e.g. gloss, to the composition. The colorant can be added to the coating in any suitable form, such as discrete particles, dispersions, solutions and/or flakes. A single colorant or a mixture of two or more colorants can be used in the coatings of the present invention. Particularly suitable for packaging coatings are those approved for food contact, such as titanium dioxide; iron oxides, such as black iron oxide; aluminum paste; aluminum powder such as aluminum flake; carbon black; ultramarine blue; phthalocyanines, such as phthalocyanine blue and phthalocyanine green; graphite fibrils; ferried yellow; quindo red; and combinations thereof, and those listed in Article 178.3297 of the Code of Federal Regulations, which is incorporated by reference herein.

Example colorants include matting pigments, dyes and tints, such as those used in the paint industry and/or listed in the Dry Color Manufacturers Association (DCMA), as well as special effect compositions. A colorant may include, for example, a finely divided solid powder that is insoluble but wettable under the conditions of use. A colorant can be organic or inorganic and can be agglomerated or non-agglomerated. Colorants can be incorporated into the coatings by grinding or simple mixing. Colorants can be incorporated by grinding into the coating by use of a grind vehicle, such as an acrylic grind vehicle, the use of which will be familiar to one skilled in the art.

Example pigments and/or pigment compositions include, but are not limited to, carbazole dioxazine crude pigment, azo, monoazo, disazo, naphthol AS, salt type (lakes), benzimidazolone, condensation, metal complex, isoindolinone, isoindoline and polycyclic phthalocyanine, quinacridone, perylene, perinone, diketopyrrolo pyrrole, thioindigo, anthraquinone, indanthrone, anthrapyrimidine, flavanthrone, pyranthrone, anthanthrone, dioxazine, triarylcarbonium, quinophthalone pigments, diketo pyrrolo pyrrole red ("DPPBO red"), titanium dioxide, carbon black, carbon fiber, graphite, other conductive pigments and/or fillers and mixtures thereof. The terms "pigment" and "colored filler" can be used interchangeably.

Example dyes include, but are not limited to, those that are solvent and/or aqueous based such as acid dyes, azoic dyes, basic dyes, direct dyes, disperse dyes, reactive dyes, solvent dyes, sulfur dyes, mordant dyes, for example, bismuth vanadate, anthraquinone, perylene aluminum, quinacridone, thiazole, thiazine, azo, indigoid, nitro, nitroso, oxazine, phthalocyanine, quinoline, stilbene, and triphenyl methane.

Example tints include, but are not limited to, pigments dispersed in water-based or water-miscible carriers such as AQUA-CHEM 896 commercially available from Degussa, Inc., CHARISMA COLORANTS and MAXITONER INDUSTRIAL COLORANTS commercially available from Accurate Dispersions division of Eastman Chemicals, Inc.

As noted above, the colorant can be in the form of a dispersion including, but not limited to, a nanoparticle dispersion. Nanoparticle dispersions can include one or more highly dispersed nanoparticle colorants and/or colorant particles that produce a desired visible color and/or opacity and/or visual effect. Nanoparticle dispersions can include colorants such as pigments or dyes having a particle size of less than 150 nm, such as less than 70 nm, or less than 30 nm. Nanoparticles can be produced by milling stock organic or inorganic pigments with grinding media having a particle size of less than 0.5 mm. Example nanoparticle dispersions and methods for making them are identified in U.S. Pat. No. 6,875,800 B2, which is incorporated herein by reference. Nanoparticle dispersions can also be produced by crystallization, precipitation, gas phase condensation, and chemical attrition (i.e., partial dissolution). In order to minimize re-agglomeration of nanoparticles within the coating, a dispersion of resin-coated nanoparticles can be used. As used herein, a "dispersion of resin-coated nanoparticles" refers to a continuous phase in which is dispersed discreet "composite microparticles" that comprise a nanoparticle and a resin coating on the nanoparticle. Example dispersions of resin-coated nanoparticles and methods for making them are described, for example, in U.S. Pat. No. 7,605,194 at column 3, line 56 to column 16, line 25, the cited portion of which being incorporated herein by reference.

Example special effect compositions that may be used include pigments and/or compositions that produce one or more appearance effects such as reflectance, pearlescence, metallic sheen, phosphorescence, fluorescence, photochromism, photosensitivity, thermochromism, goniochromism and/or color-change. Additional special effect compositions can provide other perceptible properties, such as opacity or texture. For example, special effect compositions can produce a color shift, such that the color of the coating changes when the coating is viewed at different angles. Example color effect compositions are identified in U.S. Pat. No. 6,894,086, incorporated herein by reference. Additional color effect compositions can include transparent coated mica and/or synthetic mica, coated silica, coated alumina, a transparent liquid crystal pigment, a liquid crystal coating, and/or any composition wherein interference results from a refractive index differential within the material and not because of the refractive index differential between the surface of the material and the air.

A photosensitive composition and/or photochromic composition, which reversibly alters its color when exposed to one or more light sources, can be used in the coating of the present invention. Photochromic and/or photosensitive compositions can be activated by exposure to radiation of a specified wavelength. When the composition becomes excited, the molecular structure is changed and the altered structure exhibits a new color that is different from the original color of the composition. When the exposure to radiation is removed, the photochromic and/or photosensitive composition can return to a state of rest, in which the original color of the composition returns. For example, the photochromic and/or photosensitive composition can be colorless in a non-excited state and exhibit a color in an excited state. Full color-change can appear within milliseconds to several minutes, such as from 20 seconds to 60 seconds. Example photochromic and/or photosensitive compositions include photochromic dyes.

The photosensitive composition and/or photochromic composition can be associated with and/or at least partially bound to, such as by covalent bonding, a polymer and/or polymeric materials of a polymerizable component. In contrast to some coatings in which the photosensitive composition may migrate out of the coating and crystallize into the substrate, the photosensitive composition and/or photochromic composition associated with and/or at least partially bound to a polymer and/or polymerizable component in accordance with the present invention, have minimal migration out of the coating. Example photosensitive compositions and/or photochromic compositions and methods for making them are identified in U.S. Pat. No. 8,153,344, and incorporated herein by reference.

In general, the colorant can be present in any amount sufficient to impart the desired visual and/or color effect. The colorant may comprise from 1 to 65 weight percent of the present compositions, such as from 3 to 40 weight percent or 5 to 35 weight percent, with weight percent based on the total weight of the compositions.

An "abrasion resistant particle" is one that, when used in a coating, will impart some level of abrasion resistance to the coating as compared with the same coating lacking the particles. Suitable abrasion resistant particles include organic and/or inorganic particles. Examples of suitable organic particles include but are not limited to diamond particles, such as diamond dust particles, and particles formed from carbide materials; examples of carbide particles include but are not limited to titanium carbide, silicon carbide and boron carbide. Examples of suitable inorganic particles include, but are not limited to silica; alumina; alumina silicate; silica alumina; alkali aluminosilicate; borosilicate glass; nitrides including boron nitride and silicon nitride; oxides including titanium dioxide and zinc oxide; quartz; nepheline syenite; zircon such as in the form of zirconium oxide; buddeluyite; and eudialyte. Particles of any size can be used, as can mixtures of different particles and/or different sized particles. For example, the particles can be microparticles, having an average particle size of 0.1 to 50, 0.1 to 20, 1 to 12, 1 to 10, or 3 to 6 microns, or any combination within any of these ranges. The particles can be nanoparticles, having an average particle size of less than 0.1 micron, such as 0.8 to 500, 10 to 100, or 100 to 500 nanometers, or any combination within these ranges.

Any slip agent can be used according to the present invention such as those commercial available from BYK Chemie or Dow Corning. A wax can also be used such as polyolefin wax, carnuba wax, polytetrafluoroethylene ("PTFE"), Fischer Tropsch wax, silicone or paraffin.

The hydroxy functional alkyl carbamates, and/or the compositions of the present invention, may be substantially free, may be essentially free and/or may be completely free of bisphenol A and epoxy compounds derived from bisphenol A ("BPA"), such as bisphenol A diglycidyl ether ("BADGE"). Such compounds are sometimes referred to as "BPA non intent" because BPA, including derivatives or residues thereof, are not intentionally added but may be present in trace amounts because of impurities or unavoidable contamination from the environment. The hydroxy functional alkyl carbamates and/or coatings can also be substantially free and may be essentially free and/or may be completely free of bisphenol F ("BPF") and epoxy compounds derivatived from bisphenol F, such as bisphenol F diglycidyl ether ("BFDGE"). The term "substantially free" as used in this context means the carbamates and/or coatings contain less than 1000 parts per million (ppm), "essentially free" means less than 100 ppm and "completely free" means less than 20 parts per billion (ppb) of any of the above mentioned compounds, derivatives or residues thereof.

In addition, the hydroxy functional alkyl carbamates and/or the compositions of the present invention may be substantially free, may be essentially free and/or may be completely free of formaldehyde and/or phenolic crosslinker, such as phenolic resin. The term "substantially free" as used in this context means the carbamates and/or coatings contain, and/or release on cure, less than 1000 parts per million (ppm), "essentially free" means less than 100 ppm and "completely free" means less than 100 parts per billion (ppb) of formaldehyde compounds, phenolics or derivatives or residues thereof.

The present compositions can be applied to any substrates known in the art, for example, automotive substrates, marine substrates, industrial substrates, heavy duty equipment, packaging substrates, lumber, wood flooring and furniture, apparel, electronics including housings and circuit boards and including consumer electronics such as housings for computers, notebooks, smartphones, tablets, televisions, gaming equipment, computer equipment, computer accessories, MP3 players, and the like, glass and transparencies, sports equipment including golf balls, and the like. These substrates can be, for example, metallic or non-metallic. Metallic substrates include tin, steel, tin-plated steel, chromium passivated steel, galvanized steel, aluminum, and aluminum foil. Metal sheet as used herein refers to flat metal sheet and coiled metal sheet, which is coiled, uncoiled for coating and then re-coiled for shipment to a manufacturer. Non-metallic substrates include polymeric, plastic, polyester, polyolefin, polyamide, cellulosic, polystyrene, polyacrylic, poly(ethylene naphthalate), polypropylene, polyethylene, nylon, EVOH, polylactic acid, other "green" polymeric substrates, poly(ethyleneterephthalate) ("PET"), polycarbonate, polycarbonate acrylobutadiene styrene ("PC/ABS"), polyamide, wood, veneer, wood composite, particle board, medium density fiberboard, cement, stone, glass, paper, cardboard, textiles, leather both synthetic and natural, and the like. The substrate can be one that has been already treated in some manner, such as to impart visual and/or color effect. Suitable substrates can include those in which powder coatings are typically applied.

The compositions of the present invention can be applied by any means standard in the art, such as electrocoating, spraying, electrostatic spraying, dipping, rolling, brushing, and the like.

The compositions can be applied to a dry film thickness of 0.04 mils to 4 mils, such as 0.3 to 2 or 0.7 to 1.3 mils. The compositions can also be applied to a dry film thickness of 0.1 mils or greater, 0.5 mils or greater 1.0 mils or greater, 2.0 mils or greater, 5.0 mils or greater, or even thicker. In some applications, a dry film thickness of 1-20 microns, such as 2-6 microns, is desired. In some applications, a dry-film thickness of 10-100 microns, such as 50-77 microns, might be desired. In other applications, such as when powder coatings are used, a dry film thickness of 0.5 to 50 mils, such as 1.5 to 8 mils or 2 to 4 mils, might be desired.

The compositions of the present invention can be used alone, or in combination with one or more other compositions, such as a coating system having two or more layers. For example, the compositions of the present invention can comprise a colorant or not and can be used as a primer, basecoat, and/or top coat. A "primer" will be understood as an undercoat or a coating typically applied to a surface prior to the decorating coating. For substrates coated with multiple coatings, one or more of those coatings can be coatings as described herein. The present coatings can also be used as a packaging "size" coating, wash coat, spray coat, end coat, and the like.

It will be appreciated that the compositions described herein can be either one component ("1K"), or multi-component compositions such as two component ("2K") or more. A 1K composition will be understood as referring to a composition wherein all the coating components are maintained in the same container after manufacture, during storage, etc. A 1K composition can be applied to a substrate and cured by any conventional means, such as by heating, forced air, and the like. The present compositions can also be multi-component, which will be understood as compositions in which various components are maintained separately until just prior to application. As noted above, the present compositions can be thermoplastic or thermosetting.

The composition can be a clearcoat. A clearcoat will be understood as a coating that is substantially transparent or translucent. A clearcoat can therefore have some degree of color, provided it does not make the clearcoat opaque or otherwise affect, to any significant degree, the ability to see the underlying substrate. The clearcoats of the present invention can be used, for example, in conjunction with a pigmented basecoat. The clearcoat can be formulated as is known in the coatings art.

The composition may also comprise a colorant, such as a pigmented basecoat used in conjunction with a clearcoat, or as a monocoat. A monocoat may be pigmented and used without a clearcoat on top. A suitable use of the present compositions is as a pigmented monocoat, where R is an acid functional polymer, with optional hydroxy functionality, having an Mn of 1,000 to 50,000. Another particularly suitable use of the present compositions is as a pigmented, two coat system where the first coat is not cured prior to application of the second coat; the two coats can then be cured together (and additional coats could also be applied both before and after cure). Such procedure is often referred to as a "wet-on-wet" process when the coatings are liquid, and "dust-on-dust" when the coatings are powder. The compositions of the present invention can be in one or both of the layers in the two coat system. The compositions of the present invention, when used in such a process, might have a mixture of hydroxy functional alkyl carbamates. Mixtures of compositions of the present invention are not limited to this application, and can be used according to any aspect of the invention.

Coatings as described herein are used in various industries to impart a decorative and/or protective finish. For example, such a coating or coating system may be applied to a vehicle. "Vehicle" is used herein in its broadest sense and includes all types of vehicles, such as but not limited to cars, trucks, buses, tractors, harvesters, other farm equipment, vans, golf carts, motorcycles, bicycles, railroad cars, airplanes, helicopters, ships and boats of all sizes and the like. It will be appreciated that the portion of the vehicle that is coated according to the present invention may vary depending on why the coating is being used. For example, anti-chip primers may be applied to some of the portions of the vehicle. When used as a colored basecoat or monocoat, the present coatings will typically be applied to those portions of the vehicle that are visible such as, when the vehicle is a car or truck, the roof, hood, doors trunk lid and the like, but may also be applied to other areas such as inside the trunk, inside the door and the like especially when the compositions are formulated as sealants or adhesives; for example, the compositions can be formulated so as to have a viscosity of 80,000 cps to 120,000 cps as measured by a Brookfield viscometer using spindle number 7 at 20 rpm speed and applied to the floor pan of the passenger compartment, deck lid and roof with, for example, a 2-4 mm film thickness to provide sound and/or vibration damping to a vehicle (a "sound damping composition"). The present compositions can also be applied to those portions of the vehicle that are in contact with the driver and/or passengers, such as the steering wheel, dashboard, gear shift, controls, door handle and the like. Clearcoats will typically be applied to the exterior of a vehicle.

The compositions of the present invention can also be used in the manufacture of wood products, such as particle board or fiber board, such as MDF fiber board. For example, a composition comprising a compound having a hydroxy functional alkyl carbamate according to the present invention can be used in a composition with a resin, such as an acrylic latex. The composition can be further mixed with particulate wood such as saw dust and/or wood fiber ("wood particles"), and the mixture pressed between hot plates to form the product. Such formation processes are standard in the art, and the appropriate temperatures, pressures, and formulating parameters will be ascertainable by one skilled in the art. Accordingly, the present invention is further directed to a substrate formed with the above hydroxy functional alkyl carbamate composition of the present invention and wood particles. "Formed with" in this context means that the composition comprising a hydroxy functional alkyl carbamate serves as one of the building blocks of the substrate itself, as opposed to forming a coating on the substrate.

The compositions of the present invention are also suitable for use as packaging coatings. The application of various pretreatments and coatings to packaging is well established. Such treatments and/or coatings, for example, can be used in the case of metal cans, wherein the treatment and/or coating is used to retard or inhibit corrosion, provide a decorative coating, provide ease of handling during the manufacturing process, and the like. Coatings can be applied to the interior of such cans to prevent the contents from contacting the metal of the container. Contact between the metal and a food or beverage, for example, can lead to corrosion of a metal container, which can then contaminate the food or beverage. This is particularly true when the contents of the can are acidic in nature. The coatings applied to the interior of metal cans also help prevent corrosion in the headspace of the cans, which is the area between the fill line of the product and the can lid; corrosion in the headspace is particularly problematic with food products having a high salt content. Coatings can also be applied to the exterior of metal cans. Certain coatings of the present invention are particularly applicable for use with coiled metal stock, such as the coiled metal stock from which the ends of cans are made ("can end stock"), and end caps and closures are made ("cap/closure stock"). Since coatings designed for use on can end stock and cap/closure stock are typically applied prior to the piece being cut and stamped out of the coiled metal stock, they are typically flexible and extensible. For example, such stock is typically coated on both sides. Thereafter, the coated metal stock is punched. For can ends, the metal is then scored for the "pop-top" opening and the pop-top ring is then attached with a pin that is separately fabricated. The end is then attached to the can body by an edge rolling process. A similar procedure is done for "easy open" can ends. For easy open can ends, a score substantially around the perimeter of the lid allows for easy opening or removing of the lid from the can, typically by means of a pull tab. For caps and closures, the cap/closure stock is typically coated, such as by roll coating, and the cap or closure stamped out of the stock; it is possible, however, to coat the cap/closure after formation. Coatings for cans subjected to relatively stringent temperature and/or pressure requirements should also be resistant to popping, corrosion, blushing and/or blistering.

Accordingly, the present invention is further directed to a package coated at least in part with any of the coating compositions described above. A "package" is anything used to contain another item, particularly for shipping from a point of manufacture to a consumer, and for subsequent storage by a consumer. A package will be therefore understood as something that is sealed so as to keep its contents free from deterioration until opened by a consumer. The manufacturer will often identify the length of time during which the food or beverage will be free from spoilage, which typically ranges from several months to years. Thus, the present "package" is distinguished from a storage container or bakeware in which a consumer might make and/or store food; such a container would only maintain the freshness or integrity of the food item for a relatively short period. "Package" as used herein means the complete package itself or any component thereof, such as an end, lid, cap and the like. For example, a "package" coated with any of the coating compositions described herein might include a metal can in which only the can end or a portion thereof is coated. A package according to the present invention can be made of metal or non-metal, for example, plastic or laminate, and be in any form. An example of a suitable package is a laminate tube. Another example of a suitable package is a metal can. The term "metal can" includes any type of metal can, container or any type of receptacle or portion thereof that is sealed by the food/beverage manufacturer to minimize or eliminate spoilage of the contents until such package is opened by the consumer. One example of a metal can is a food can; the term "food can(s)" is used herein to refer to cans, containers or any type of receptacle or portion thereof used to hold any type of food and/or beverage. "Beverage can" may also be used to refer more specifically to a food can in which a beverage is packaged. The term "metal can(s)" specifically includes food cans (including beverage cans) and also specifically includes "can ends" including "E-Z open ends", which are typically stamped from can end stock and used in conjunction with the packaging of food and beverages. The term "metal cans" also specifically includes metal caps and/or closures such as bottle caps, screw top caps and lids of any size, lug caps, and the like. The metal cans can be used to hold other items as well, including, but not limited to, personal care products, bug spray, spray paint, and any other compound suitable for packaging in an aerosol can. The cans can include "two piece cans" and "three-piece cans" as well as drawn and ironed one-piece cans; such one piece cans often find application with aerosol products. Packages coated according to the present invention can also include plastic bottles, plastic tubes, laminates and flexible packaging, such as those made from PE, PP, PET and the like. Such packaging could hold, for example, food, toothpaste, personal care products and the like.

The coating can be applied to the interior and/or the exterior of the package. For example, the coating can be rollcoated onto metal used to make a three-piece metal can, can end stock and/or cap/closure stock or sprayed, flow coated, or gravure or roll coated onto a formed two piece metal can. The coating is applied to a coil or sheet by roll coating; the coating is then cured by radiation and can ends are stamped out and fabricated into the finished product, i.e. can ends. The coating could also be applied as a rim coat to the bottom of the can; such application can be by roll coating. The rim coat functions to reduce friction for improved handling and protection during the continued fabrication and/or processing of the can. The coating can be applied to the "side stripe" of a metal can, which will be understood as the seam formed during fabrication of a three piece can. The coating can also be applied to caps and/or closures; such application can include, for example, a protective varnish that is applied before and/or after formation of the cap/closure and/or a pigmented enamel post applied to the cap, particularly those having a scored seam at the bottom of the cap. Decorated can stock can also be partially coated externally with the coating described herein, and the decorated, coated can stock used to form various metal cans.

Metal coils, having wide application in many industries, are also substrates that can be coated according to the present invention. Coil coatings also typically comprise a colorant. Metal parts can also be coated according to the present invention. A metal part is a substrate made all or in part from metal that has been formed into a desired shape. Any of the substrates described herein can have sharp edges. "Sharp edge(s)" can refer to edges that have been stamped, sheared, machine cut, laser cut and the like.

The compositions of the present invention are also suitable for use as heavy duty equipment and/or general industrial powder coatings, such as in the monocoat or multicoat systems, such as two coat systems. The application of various pretreatments and coatings to heavy duty equipment or general industrial substrates is well established. Such treatments and/or coatings, for example, can be used in the case wherein the treatment and/or coating is used to retard or inhibit corrosion, provide a decorative coating, provide ease of handling during the manufacturing process, protect sharp edges and the like. The compositions of the present invention can provide electrostatic control for powder coatings, which provides additional coating protection to sharp edges that are points of corrosion failure in the field.

After application to the substrate, the coating composition may be cured by any appropriate means, for cure times and temperatures appropriate for the chemistry of the composition, the substrate being coated, and the like. In some applications a relatively low cure temperature for a relatively long time may be desired, such as a cure temperature of 140° C. to 100° C. for 60 minutes or less, such as 20 or 30 minutes. In other applications a relatively high cure temperature for a relatively short time may be desired, such as a cure temperature of 300° C. to 200° C. for a time of three minutes or less, such as two minutes or less, or one minute or less, or 30 seconds or less or 15 seconds or less. Accordingly, the present coatings can be used across a broad range of industries and cure conditions.

In addition to their use in compositions and substrates as described above, any of the carbamate compounds as described herein can be used in thermoplastic acid functional polymers such as polyesters, ethylene acrylic acid copolymers and terpolymers, and ionomers. In melt blends with thermoplastic polymers, the carbamate compounds can serve as additives, cross-linkers, chain extenders, to increase the hydrolysis resistance of polyesters, and to modify viscosity for applications such as extruded fibers, films, injection molded articles, extrusion coating, blow molding, extrusion blowmolding, and extrusion. For example, the carbamate compounds can be added to thermoplastic compositions such as nylon, pvdf compositions, polyesters, polyolefins, PVC, PVA, acrylic and the like. The hydroxy functional alkyl carbamates described herein can also be used in applications currently employing carbodiimide additives.

As used herein, unless otherwise expressly specified, all numbers such as those expressing values, ranges, amounts or percentages may be read as if prefaced by the word "about", even if the term does not expressly appear. Also, any numerical range recited herein is intended to include all sub-ranges subsumed therein. Singular encompasses plural and vice versa. For example, although reference is made herein to "a" hydroxy functional alkyl carbamate, "a" film-forming resin, "an" isocyanate, "an" alkanol amine, "the" residue of "an", and the like, one or more of each of these and any other components can be used. As used herein, the term "polymer" refers to oligomers and both homopolymers and copolymers, and the prefix "poly" refers to two or more. Including, for example and like terms means including for example but not limited to. When ranges are given, any endpoints of those ranges and/or numbers within those ranges can be combined within the scope of the present invention. The word "comprising" and forms of the word "comprising", as used in this description and in the claims, does not limit the present invention to exclude any variants or additions. Additionally, although the present invention has been described in terms of "comprising", the processes, materials, and coating compositions detailed herein may also be described as "consisting essentially of" or "consisting of".

Non-limiting aspects of the invention include:
1. A hydroxy functional alkyl carbamate having the formula:

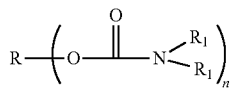

wherein R comprises a substituted or unsubstituted $C_1$ to $C_{36}$ alkyl group, an aromatic group, and/or a polymeric moiety; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6.

2. The carbamate of aspect 1, wherein at least one R1 comprises a 2-hydroxyethyl or 2-hydroxypropyl group.

3. The carbamate of any preceding aspect, wherein the R1 groups do not contain an ether linkage.

4. The carbamate of any preceding aspect, wherein R comprises ether.

5. The carbamate of any preceding aspect, wherein R comprises polyurethane.

6. A composition comprising a film-forming resin and hydroxy functional alkyl carbamate crosslinker having the formula

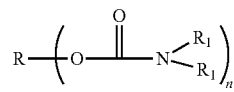

wherein R comprises a substituted or unsubstituted $C_1$ to $C_{36}$ alkyl group, an aromatic group, and/or a polymeric moiety; wherein each $R_1$ is independently a hydrogen, alkyl having at least 1 carbon, or a hydroxy functional alkyl having 2 or more carbons and at least one $R_1$ is a hydroxy functional alkyl having 2 or more carbons; and n is 2-6.

7. The composition of aspect 6, wherein R comprises a substituted or unsubstituted $C_2$-$C_{12}$ alkyl group, such as a substituted or unsubstituted $C_6$ alkyl group or a $C_2$ alkyl group.

8. The composition of aspect 6 or 7, wherein $R_1$ and R are defined as in any of aspects 2 through 5.

9. The composition of any of aspects 6 to 8, wherein the hydroxy functional alkyl carbamate crosslinker is selected from a hydroxy functional alkyl carbamate crosslinker according to any of aspects 1-5.

10. The composition of any of aspects 6 to 9, wherein the composition is substantially, essentially and/or completely free of BPA.

11. The composition of any of aspects 6 to 10, wherein the coating is substantially, essentially and/or completely formaldehyde free and/or phenolic free.

12. The composition of any of aspects 6 to 11, wherein the composition is formulated as a coating composition, such as a powder coating composition.

13. The composition of any of aspects 6 to 12, further comprising a catalyst, such as a tin and/or titanium containing catalyst.

14. The composition of any of aspects 6 to 13, comprising 2 or more different hydroxy functional alkyl carbamates.

15. The composition of any of aspects 6 to 14, wherein the film-forming resin comprises polyurethane, acrylic latex, such as one having an acid value of 10 to 15 mg KOH/g, or 10 mg KOH/g or greater; polyurethane acrylic latex; an acrylic resin; polyester; an epoxy resin; and/or a polyolefin, such as a polyolefin dispersion.

16. The composition of any of aspects 6 to 15, wherein the composition is formulated as a sound damping composition.

17. The composition of any of aspects 6 to 16, wherein R does not comprise functional groups, or R does not comprise epoxy groups or R does not comprise hydroxy groups.

18. A substrate coated at least in part with the composition of any of aspects 6 to 17.

19. The substrate of aspect 18, wherein the substrate is selected from a package, a metal can, a metal part and a vehicle or has sharp edges.

20. The substrate of aspect 18, wherein the substrate comprises rubber or plastic or a metal sheet or coil.

21. A substrate formed with a hydroxy functional alkyl carbamate of any preceding aspect.

22. The substrate of aspect 21, wherein the substrate is a wood product, such as particle board or fiber board.

EXAMPLES

The following examples are intended to illustrate the invention and should not be construed as limiting the invention in any way.

Example A

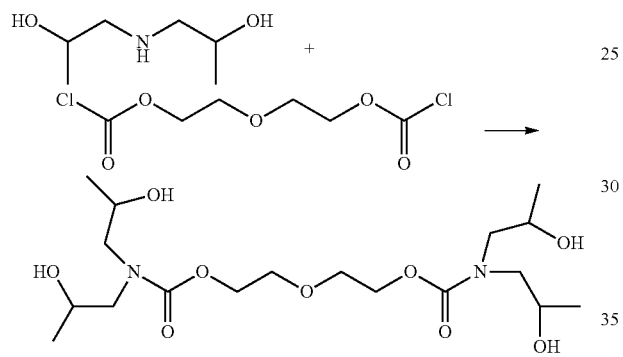

ketone (239 g, commercial available from Dow Chemical Co), and sodium carbonate (116.38 g, and commercial available from Sigma Aldrich). Agitation and a nitrogen flow of 0.2 scft/min ("scft" means standard cubic feet) were started. The reaction mixture was cooled to 0° C. by using an ice bath. Diethylene glycol bischloroformate (31.19 g, 0.270 mol, commercially available from Axiall) was added into the reaction mixture drop wise over 1.5 hours to keep the reaction temperature below 5° C. After completion of addition, the reaction temperature was held around 5° C. for 2 hours. The mixture was slowly warmed to room temperature and stirring maintained at room temperature for 24 hours. The reaction mixture was filtered through a filter paper and the solid washed with MEK (31 g). The filtrate was collected and transferred to a flask. The solvent was removed by vacuum distillation and a clear viscous liquid was obtained.

Example B

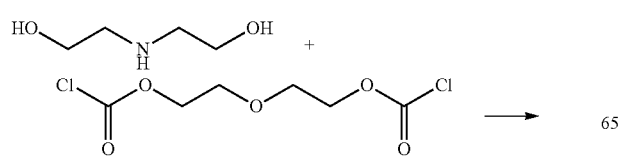

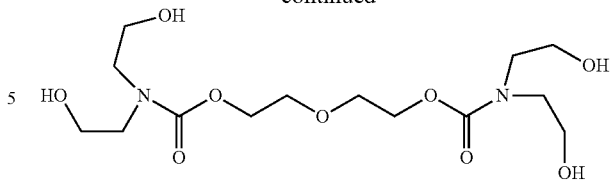

Synthesis of Tetrakis (2-hydroxyethyl) Carbamate

Into a 1000-mililiter, 4-necked flask equipped with a stirrer, a condenser, a nitrogen inlet, and a thermocouple in cooling bath, was charged diethanolamine (64.1 g, and commercial available from Dow Chemical Co), acetone (385 g), and sodium carbonate (194.0 g, commercial available from Sigma Aldrich). Agitation and a nitrogen flow of 0.2 scft/min ("scft" means standard cubic feet) were started. The reaction mixture was cooled to 0° C. by using an ice bath. Diethylene glycol bischloroformate (63.42 g, commercially available from Axiall) was added into the reaction mixture drop wise over 3 hours to keep the reaction temperature below 5° C. After completion of addition, the reaction temperature was held around 5° C. for 2 hours. The reaction mixture was slowly warmed to room temperature and stirring maintained at room temperature for 24 hours. The reaction mixture was filtered through a filter paper and the solid washed with acetone (63.6 g). The filtrate was collected and transferred to a flask. The solvent was removed by vacuum distillation and a clear viscous liquid was obtained.

Example C

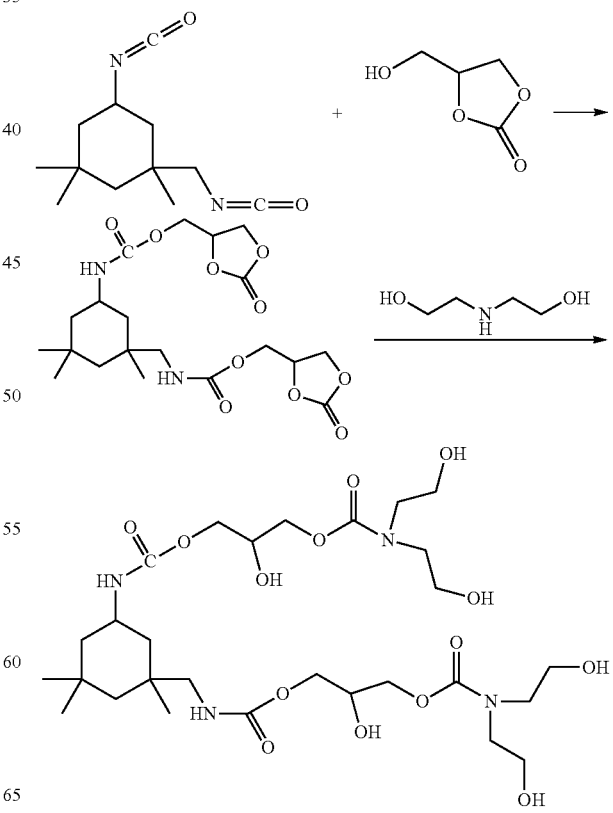

Synthesis of Tetrakis (2-hydroxyethyl) Carbamate

Into a 1000-mililiter, 4-necked flask equipped with a stirrer, a condenser, a nitrogen inlet, and a thermocouple in a heating mantle, was charged IPDI (111.1 g, commercial available from Covestro), methyl isobutyl ketone (111.1 g, commercial available from Shell Chemical Co), and dibutyl-tin dilaurate (0.222 g, commercial available from Air products & chemicals). Agitation and a nitrogen flow of 0.2 scft/min ("scft" means standard cubic feet) were started. The reaction mixture was heated to 70° C. At 70° C., glycerol 1,2-carbonate (124.0 g, commercial available from TCI) was added into the reaction mixture drop wise over 40 minutes followed by a rinse with MIBK (20.7 g). After completion of the addition, the reaction temperature was held at 70° C. for 9 hours until the NCO peak was gone as determined by IR (ThermoScientific Nicolet iS5 FT-IR). Diethanolamine (99.9 g. commercial available from Dow Chemical Co) was added into the reaction mixture over 30 minutes and then heat to 80° C. The reaction mixture was held over 3 hours until amine MEQ was less than 0.2. (Amine MEQ filtration performed with Metrohm 888 Titrando with 0.1 N Perchloric acid in glacial acetic acid.) Dowanol PM (63 g, commercial available from Dow Chemical Co) was added into the reaction mixture and the reaction mixture was cooled to 40° C.

Example D

Acrylic Latex Preparation

To a 5 L four-neck reaction flask was added the following: 223.5 g PRIMACOR 5980i (Dow Chemical), 67.5 g dimethylethanolamine (Huntsman Corporation), and 826.6 g deionized Water. The flask was then fitted with a thermocouple, water condenser, stirring blade, and a 1 SCFH Nitrogen blanket. While under agitation the contents of the flask were heated to 95° C. and held for 2 Hrs. until the mixture became visually homogeneous. The mixture was then allowed to cool to 70° C.

Added dropwise to the flask over 125 minutes was a mixture of 5.3 g of 35% Hydrogen Peroxide (purchased from Sigma Aldrich) and 105.2 g Deionized Water. Five minutes later a separate feed was added to the flask dropwise over 2 Hrs., which contained a mixture of acrylic monomers: 5.2 g Benzoin (Sigma Aldrich) 247.4 g Ethyl Acrylate (Arkema), 15.8 g Glycidyl methacrylate (Dow Chemical), 263.2 g Methyl Methacrylate (Evonik), and 26.3 g Dowanol PM (Dow Chemical). After both feeds were finished, the latex was held for 30 minutes. A mixture of 0.89 g of 35% Hydrogen Peroxide and 17.8 g Deionized Water was then added and the latex was held for 30 minutes. Another mixture of 0.89 g of 35% Hydrogen Peroxide and 17.80 g Deionized Water was then added and the latex held for 60 minutes. After the 60 minute hold, the latex was warmed to 80° C. and then held for 60 minutes. After the 60 minute hold the resin was allowed to cool to less than 60° C. The final product was filtered using a 5 m filer bag. The final latex had a measured solid content of 29.8% (ASTM D2369—10(2015) e1 "Standard Test Method for Volatile Content of Coatings") and a theoretical acid value of 13.7 mg KOH/g.

The hydroxyl functional alkyl carbamates of Example A and Example B were each mixed with the acrylic latex polymer of Example D and a measured acid value of 12.8 mg KOH/g. The crosslinkers of Example A and Example B were added in various amounts to achieve different ratios of COOH/OH as indicated in Table 1. To the mixtures were added 10% on solids of ethylene glycol mono-2-ethylhexyl ether (purchased from Eastman as Ektasolve EEH). The mixtures were drawn down on 0.0082" zirconium pretreated aluminum substrate. The film was baked for 10 seconds in a 290° C. conveyor oven. The substrate reached a Peak Metal Temperature of 232.2° C. The final dry film weight was 0.32 mils.

After baking, the cured coatings were tested for solvent resistance using the "MEK Double Rub" test. The MEK double rub test rub used a rag that was saturated with Methyl Ethyl Ketone. The coatings were evaluated for the number of double rubs it took to soften and break through the coating or until 100 double rubs were performed.

As shown in the following table, the solvent resistance (MEK DR) improved when using the crosslinkers of the present invention. This indicates that the crosslinker used provides better solvent resistance than coatings lacking the hydroxy functional alkyl carbamate crosslinker.

TABLE 1

| COOH:OH Ratio | Hydroxyl Functional Alkyl Carbamate Crosslinker | MEK DR |
|---|---|---|
| Acrylic Latex Alone | none | 16 |
| 1:0.35 | Example A | 24 |
| 1:0.55 | | 24 |
| 1:0.90 | | 38 |
| 1:0.35 | Example B | 21 |
| 1:0.55 | | 24 |
| 1:0.90 | | 23 |

Whereas particular embodiments of this invention have been described above for purposes of illustration, it will be evident to those skilled in the art that numerous variations of the details of the present invention may be made without departing from the invention as defined in the appended claims.

What is claimed is:

1. A composition comprising:
   a. an acid functional film-forming resin; and
   b. a hydroxy functional alkyl carbamate crosslinker having the formula:

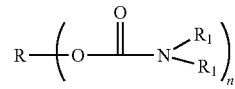

wherein R comprises a substituted or unsubstituted $C_1$ to $C_{36}$ alkyl group, an aromatic group, and/or a polymeric moiety; wherein each $R_1$ is independently a hydroxy functional alkyl having 2 or more carbons; and n is 2-6, wherein the acid functional film-forming resin comprises acid functional groups which, upon cure, crosslink with the functionality of the hydroxy functional alkyl carbamate crosslinker, and wherein the composition is substantially formaldehyde free.

2. The composition of claim 1, wherein R comprises a substituted or unsubstituted $C_2$-$C_{12}$ alkyl or aromatic group.

3. The composition of claim 1, wherein $R_1$ comprises a 2-hydroxyethyl or 3-hydroxypropyl group.

4. The composition of claim 1, wherein R further comprises an ether.

5. The composition of claim 1, wherein R comprises a polyurethane.

6. The composition of claim 1, wherein R does not comprise functional groups.

7. The composition of claim 1, wherein R does not comprise epoxy groups.

8. The composition of claim 1, wherein R does not comprise hydroxy groups.

9. The composition of claim 1, wherein the acid functional film-forming resin comprises an acid functional polyolefin dispersion.

10. The composition of claim 1, wherein the acid functional film-forming resin comprise a polyurethane resin, an acrylic resin, a polyester resin, an epoxy resin and/or a polyolefin.

11. The composition of claim 1, wherein the composition is a powder coating composition.

12. The composition of claim 1, further comprising a catalyst.

13. The composition of claim 1, further comprising water and/or an organic solvent.

14. A coating comprising the composition of claim 1.

15. A substrate coated at least in part with the coating of claim 14.

16. The substrate of claim 15, wherein the substrate comprises a package.

17. The substrate of claim 15, wherein the substrate comprises a metal can.

18. The substrate of claim 15, wherein the substrate comprises a vehicle.

19. The substrate of claim 15, wherein the substrate comprises metal sheet or coil.

20. A sound damping composition comprising the composition of claim 1.

* * * * *